United States Patent
Lichter et al.

(10) Patent No.: US 8,917,576 B2
(45) Date of Patent: Dec. 23, 2014

(54) REMOTE FLOODED MEMBER DETECTION

(75) Inventors: Harry J. Lichter, Palm Beach Gardens, FL (US); Joseph M. Cuschieri, Boca Raton, FL (US)

(73) Assignee: Lockheed Martin Corporation, Bethesda, MD (US)

( * ) Notice: Subject to any disclaimer, the term of this patent is extended or adjusted under 35 U.S.C. 154(b) by 453 days.

(21) Appl. No.: 13/279,745

(22) Filed: Oct. 24, 2011

(65) Prior Publication Data

US 2012/0099398 A1 Apr. 26, 2012

Related U.S. Application Data

(60) Provisional application No. 61/406,479, filed on Oct. 25, 2010.

(51) Int. Cl.
| | | |
|---|---|---|
| *G01S 15/00* | (2006.01) | |
| *G01N 29/07* | (2006.01) | |
| *G01S 7/539* | (2006.01) | |
| *G01S 15/88* | (2006.01) | |

(52) U.S. Cl.
CPC .............. *G01S 7/539* (2013.01); *G01N 29/07* (2013.01); *G01S 15/88* (2013.01)
USPC ................ 367/93; 367/87; 340/618; 340/612

(58) Field of Classification Search
USPC .............................. 367/93, 87; 340/618, 612
See application file for complete search history.

(56) References Cited

U.S. PATENT DOCUMENTS

| | | | |
|---|---|---|---|
| 4,001,764 A * | 1/1977 | Holland et al. .................... 367/6 |
| 4,445,363 A * | 5/1984 | Bennett et al. ............. 73/40.5 A |
| 4,481,818 A * | 11/1984 | Hellqvist ......................... 73/587 |
| 4,502,041 A * | 2/1985 | Penzien ......................... 340/532 |
| 4,628,737 A * | 12/1986 | Charles et al. .................. 73/624 |
| 5,062,089 A | 10/1991 | Willard et al. |
| 6,595,035 B1 * | 7/2003 | Maley .......................... 73/19.03 |
| 6,914,530 B2 * | 7/2005 | Geary ........................... 340/604 |
| 2004/0174770 A1 | 9/2004 | Rees |
| 2008/0316862 A1 | 12/2008 | Bernecky et al. |
| 2010/0162818 A1 * | 7/2010 | David et al. ..................... 73/592 |

OTHER PUBLICATIONS

International Search Report for international application No. PCT/US2011/057496, dated Jan. 30, 2012 (2 pages).
Written Opinion of the International Searching Authority for international application No. PCT/US2011/057496, dated Jan. 30, 2012 (5 pages).
U.S. Appl. No. 13/280,490, filed Oct. 25, 2011 (18 pages).
U.S. Appl. No. 13/280,536, filed Oct. 25, 2011 (19 pages).
U.S. Appl. No. 13/280,843, filed Oct. 25, 2011 (19 pages).
U.S. Appl. No. 13/280,914, filed Oct. 25, 2011 (24 pages).

(Continued)

*Primary Examiner* — George Bugg
*Assistant Examiner* — Naomi Small
(74) *Attorney, Agent, or Firm* — Hamre, Schumann, Mueller & Larson, P.C.

(57) ABSTRACT

Utilizing a sonar system to determine if a structural member of an underwater support structure that is supposed to be filled with air is instead flooded with water. The determination that a supposedly air filled structural member is instead flooded with water provides an indication that the structural member is cracked or damaged, making it easier to find damaged members and effect suitable repair. The sonar system is located a distance from the structural member so that it is spaced from the structural member.

20 Claims, 8 Drawing Sheets

(56) References Cited

OTHER PUBLICATIONS

U.S. Appl. No. 13/280,932, filed Oct. 25, 2011 (23 pages).
"Flooded Member Detection," Ashtead Technology, available online at http://ashtead-technology.com/productgroup/offshore/1252/, printed Mar. 29, 2012 (1 page).
"Flooded Member Detection," Ashtead Technology, available online at http://ashtead-technology.com/productgroup/offshore/1328/, printed Mar. 29, 2012 (1 page).
"Flooded Member Detection," Ashtead Technology, available online at http://ashtead-technology.com/productgroup/offshore/1382/, printed Mar. 29, 2012 (1 page).
"Forward Looking Navigation Sonars," FarSounder, available online at http://www.farsounder.com/products/navigation_sonars, printed Mar. 29, 2012 (3 pages).
"Tritech SeaKing Parametric Sub Bottom Profiler (SBP)," available online at http://www.tritech.co.uk/products/products-parametric/sbp.htm, printed Mar. 29, 2012, (1 page).
Reto Meier, "Flooded Member Detection," available online at http://knol.google.com/k/reto-meier/flooded-member-detection/30gnpxmrpztmf/2#, printed Mar. 29, 2012 (3 pages).
"Seaeye Lynx," available online at http://www.seaeye.com/lynx.html, printed Mar. 29, 2012 (7 pages).
"What We Do: IMR Services: Structural Inspections," Trico Marine Group, available online at http://web.archive.org/web/20100831085149/http://www.do.tricomarine.com/structural-inspections.php, dated Aug. 31, 2010, printed Mar. 30, 2012 (2 pages).
"3D Sonar Systems," FarSounder, available online at http://www.farsounder.com/files/F31566_(r2.0)_3D_Sonar_Brochure.pdf, 2010 (4 pages).

* cited by examiner

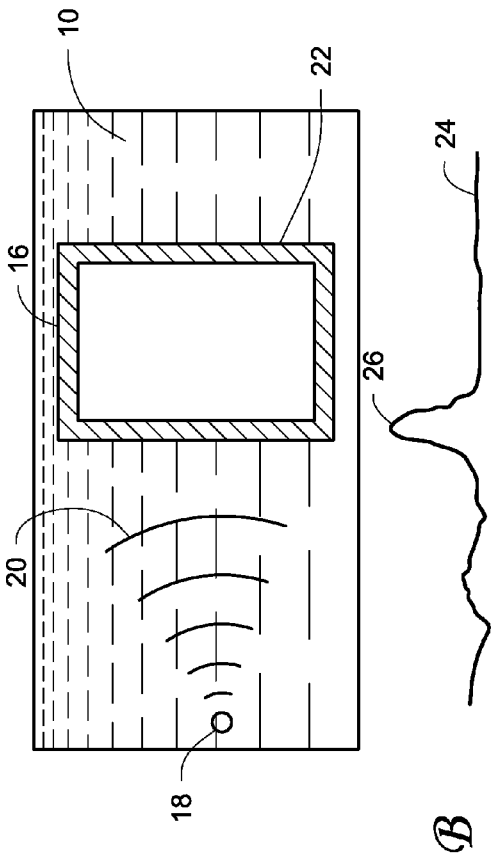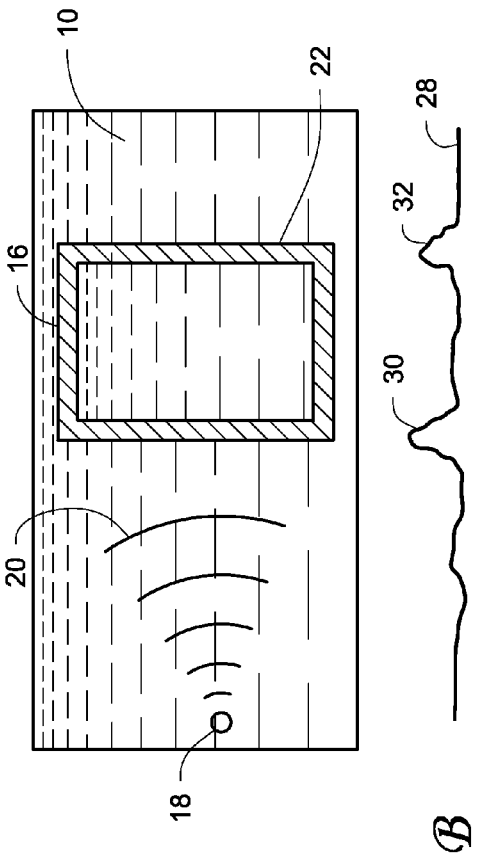
Fig. 2A  Fig. 2B  Fig. 3A  Fig. 3B

REMOTE FLOODED MEMBER DETECTION

This application claims the benefit of U.S. Provisional Application Ser. No. 61/406,479 filed on Oct. 25, 2010, the entire contents of which are incorporated herein by reference.

FIELD

This disclosure relates to a method of determining whether a structural member of an underwater support structure is filled with air or flooded with water.

BACKGROUND

A number of underwater support structures exist that need to be inspected for potential damage. One example of an underwater support structure is for an offshore platform such as an oil drilling platform. Underwater support structures of offshore platforms are often made of welded tubular members, some of which are normally water filled and some of which are normally air filled. Whether air filled or not, the tubular members have marine growth on them, making it difficult to visually inspect the tubular members for damage and cracks. When an offshore platform is stressed, for example in a hurricane, underwater inspections of the structural members must be performed. If a crack develops on an air filled member, it will flood. Identifying the flooded members during an inspection is one way of finding the cracks.

Previous methods at identifying flooded members have included the use of acoustic devices which are placed in contact with the members being inspected. One example of an acoustic device is an ultrasonic probe which when brought in contact against a structural member is set to ignore the first couple of inches, then listens for reflections from the possible steel to air or water, water to air or air to water, and water or air to steel interfaces over a pre-set range. Another inspection device that is used is a radiographic (i.e. x-ray) device which does not need to be in contact with the member, but does require close proximity, to inspect the member in a submerged environment, not to mention the difficulties with deploying X-ray underwater.

SUMMARY

A method is described that utilizes a sonar system to determine if a structural member of an underwater support structure is filled with air or water. If the structural member is supposed to be air filled but is instead flooded with water, that provides an indication that the structural member is cracked or damaged, making it easier to identify damaged members and effect suitable repair.

The sonar system is located some distance from the structural member so that it is spaced from the structural member, i.e. the sonar system is not in close proximity to or in intimate contact with the structural member or marine growth on the structural member, but is instead spaced from the structural member so that there is some distance between the sonar system and the structural member.

A flooded structural member has a different acoustic-structural response than the acoustic-structural response of an air filled structural member. By directing an acoustic signal at a structural member of interest and detecting the acoustic-structural response, the detected acoustic-structural response can then be processed to extract the acoustic-structural features. As used herein, features refers to the magnitude (i.e the various peaks and valleys) of the acoustic signal. Comparing the determined acoustic-structural features to the expected acoustic-structural features for that structural member will determine whether there is a sufficient match. Therefore, if the structural member is intended to be air filled, and the determined acoustic-structural response corresponds to a flooded structural member, a determination is made that the structural member is flooded, thereby indicating that the structural member is cracked or otherwise damaged in a manner to allow water to flood the structural member.

The sonar system can be any system that employs low to mid frequency acoustic waves. The sonar system can be, for example, a diver operated system, coupled to an autonomous underwater vehicle (AUV), a remotely operated vehicle (ROV) or other host platform vehicle, towed by a vehicle, pole mounted, or hull mounted.

In one embodiment, a method includes using a sonar system to determine if a structural member of an underwater support structure that is intended to be filled with air has flooded with water, where the sonar system is spaced some distance from the structural member so that it is not in contact with the structural member.

In another embodiment, a method of scanning an underwater support structure for flooded structural members includes directing an acoustic wave at an underwater structural member of interest that forms part of the underwater support structure from a source that is positioned at a distance from the underwater structural member of interest. An acoustic-structural response resulting from the acoustic wave incident on the underwater structural member of interest is then detected, and the detected acoustic-structural response is processed to extract the acoustic-structural features. The extracted acoustic-structural features are then compared with the expected acoustic-structural features for the underwater structural member of interest. Based on the comparison, it is determined whether the underwater structural member of interest is flooded or not.

The underwater support structure and structural member thereof can be any structural member of any underwater support structure where one may wish to inspect the support structure to determine if the structural member is flooded with water. For example, the underwater support structure can include man-made structures such as offshore oil platform support structures and the like.

As used herein, the term underwater includes any type of underwater environment in which an underwater support structure may be located and may need to be inspected including, but not limited to, salt-water locations such as seas and oceans, and freshwater locations.

DRAWINGS

FIGS. 2A and 2B depict an air filled member and the corresponding return intensity of an acoustic wave incident on the air filled member, respectively.

FIGS. 3A and 3B depict a water filled, flooded member and the corresponding return intensity of an acoustic wave incident on the flooded member, respectively.

DETAILED DESCRIPTION

Figure 1:
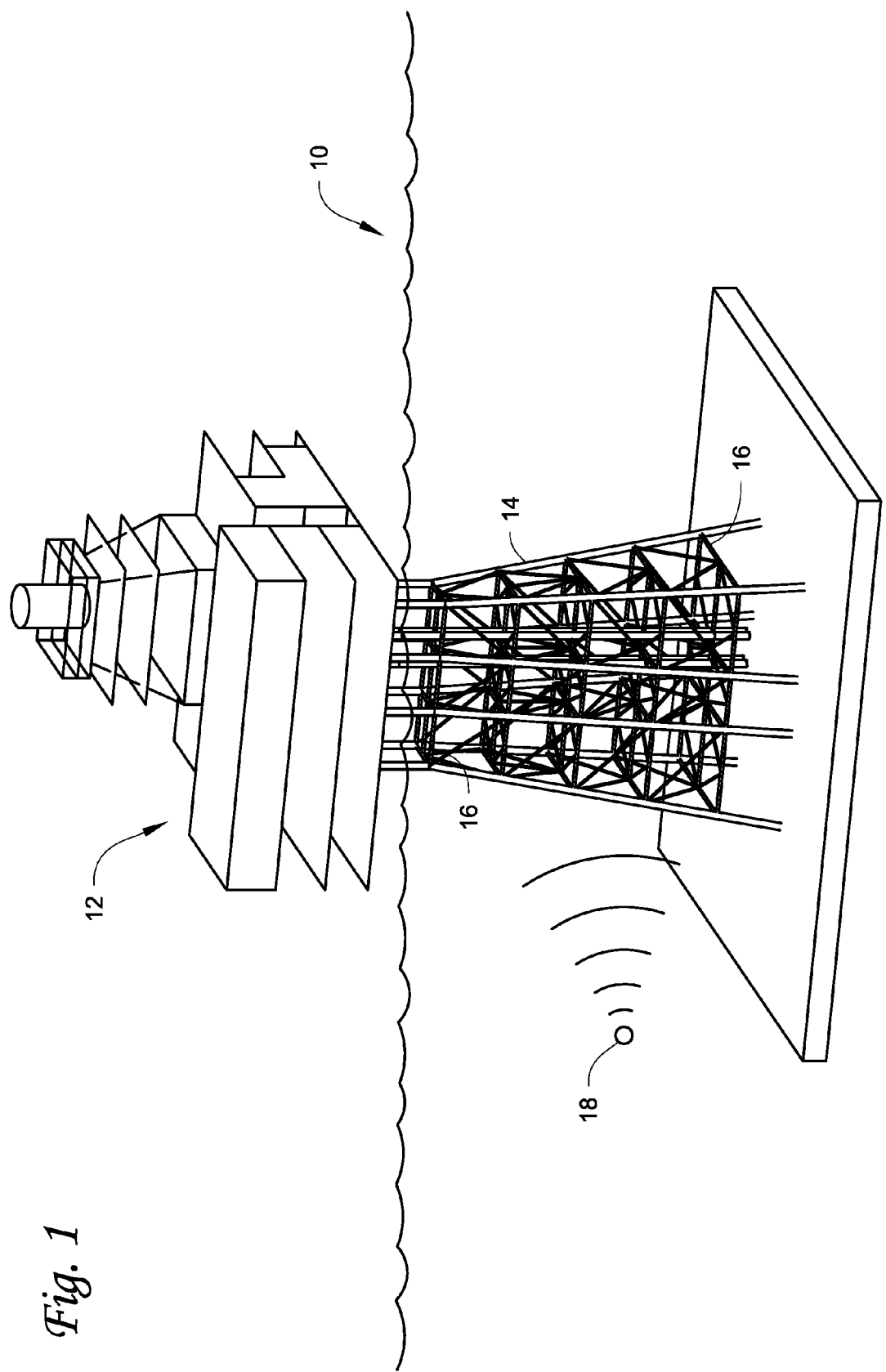
FIG. 1 depicts a typical offshore platform supported by an underwater support structure.

FIG. 1 illustrates a body of water 10 with an offshore platform 12 supported by an underwater support structure 14. The body of water 10 can be any body of water, saltwater or freshwater. In this illustrated example, the platform 12 is an oil platform, and the support structure 14 is mounted to the floor of the body of water. However, the depiction of an oil platform and associated support structure is exemplary only, and it is to be understood that the underwater support structure can be any type of underwater support structure, man-made or naturally occurring, mounted on the seafloor or floating mid-water, and the platform 12 can be other types of platforms.

The support structure 14 is composed of a number of welded or otherwise joined tubular structural members 16, some of which are intended to be normally water filled and some of which are intended to be normally air filled. As used herein, a normally water filled structural member is different than a normally air filled structural member that has cracked or has been otherwise damaged and flooded with water. To emphasize this distinction, a structural member that is intended to be normally air filled, but which for whatever reason has flooded with water, will be referred to as a flooded structural member, with the term flooded implying a condition of the structural member that deviates from its intended or normal condition. So a structural member that is intended to be water filled is not a flooded member.

A sonar system 18 is illustrated as being spaced from the support structure 14 and the individual structural members 16 so that it is not in contact with the support structure or the structural members. The phrase "not in contact" used herein means that the sonar system 18 is not in intimate contact with the support structure 14 or any of its structural members 16 or marine growth on the structural members, but is instead spaced from the support structure and its structural members so that there is some distance between the sonar system and the support structure and the structural members.

As described in further detail below, the sonar system 18 is employed to determine if a structural member of the underwater support structure 14 that is intended to be filled with air has flooded with water. The use of the sonar system 18 in this manner is based on a realization by the inventors that a flooded structural member has a different acoustic-structural response to an incident acoustic wave than the acoustic-structural response of an air filled structural member. By directing an acoustic wave at a structural member of interest and detecting the return acoustic-structural response, the detected acoustic-structural response can then be processed to extract the acoustic-structural features. Comparing the extracted acoustic-structural features to the expected acoustic-structural features for that structural member will determine whether there is a sufficient match. If the structural member is intended to be air filled, and the determined acoustic-structural response corresponds to a flooded structural member, a determination is made that the structural member is flooded, thereby indicating that the structural member is cracked or otherwise damaged in a manner to allow water to flood the structural member.

The sonar system 18 uses low to mid frequency acoustic waves that are able to penetrate and excite the skin of the structural member of interest that is being inspected. The ability of an acoustic wave to penetrate and excite a structural member depends on factors such as the material of the structural member and the thickness of the skin, i.e. the thickness of the wall of the structural member. Therefore, the frequency that is used may vary, and any frequency that would be sufficient to penetrate and excite the skin of the structural member of interest is encompassed within the meaning of low to mid frequency.

Preferably, the sonar system would be a multi-beam sonar with dual frequency, one frequency at or below 50 kHz and one frequency at or above 100 kHz. The sonar preferably has power sufficient to operate at greater than about a 50 ft. range and could be parametric or conventional type. One example of an acoustic frequency that is believed by the inventors to be suitable is 20 kHz. An example of a suitable sonar system is the SeaKing Parametric SBP sub-bottom profiler available from Tritech International Limited of Aberdeen, United Kingdom. The SeaKing Parametric SBP is a dual frequency sonar with a low frequency of 20 kHz and a primary frequency of 200 kHz. In the case of the SeaKing Parametric SBP, the sonar can be, for example, located approximately 50 feet away from the support structure while inspecting the support structure. However, the sonar system 18 could be located farther away or closer to the support structure than 50 feet. When a multi-beam sonar is used, the method described herein can simply be repeated for each of the sonar's acoustic beams.

The sonar system 18 is used to acoustically detect the difference between an air filled structural member and a water filled, flooded member. This is done by directing an acoustic signal or signal transient at a structural member of interest and detecting the acoustic-structural response return from the structural member. The acoustic-structural response return is then processed to determine the acoustic-structural features and whether the structural member is air filled or flooded. Optionally, a flooded member(s) that is detected can be indicated on a three-dimensional model of the support structure to help show the extent of any flooded members and help better understand the condition of the support structure.

With reference to FIGS. 2A-B and 3A-B, acoustic pinging of a structural member 16 by the sonar device 18 is illustrated. For the purposes of helping to explain the concept, the structural members 16 are depicted as being rectangular in cross-sectional shape. However, in practice, the structural members 16 will typically have a round (i.e. circular) cross-sectional shape. But the structural member can have any cross-sectional shape not limited to rectangular or round/circular.

FIG. 2A illustrates an air filled structural member 16, with FIG. 2B illustrating a return acoustic-structural wave 24 detected by the sonar device 18 as a result of the sonar device sending an acoustic wave 20 toward and impacting the structural member 16. The wall defining the structural member 16 is referred to herein as the skin 22 of the structural member. The wave 20 is of such frequency as to be able to penetrate and excite the skin 22. As indicated in FIG. 2B, nearly the full intensity of the acoustic wave 20 is reflected back (indicated by the amplitude 26 of the envelope of the return wave 24) as a result of the wave 20 contacting the skin 22/air interface inside the member 16.

In contrast, FIG. 3A illustrates a water filled structural member 16, with FIG. 3B illustrating a return acoustic-structural wave 28 detected by the sonar device 18 as a result of the sonar device sending the acoustic wave 20 toward and impacting the structural member 16. The acoustic wave 20 penetrates and excites the skin 22. However, because the member is water filled, the wave 20 continues on through the water in the member to the opposite wall of the member 16 and out the other side. As indicated in FIG. 3B, the return wave envelope 28 shows two smaller peaks 30, 32 indicating the skin 22/water interfaces.

As evident from FIGS. 2A-B and 3A-B, an air filled member 16 has a different acoustic-structural response than a water filled member 16. This difference in acoustic-structural response can be exploited to determine whether a member that is supposed to be air filled is instead flooded.

Figure 4:
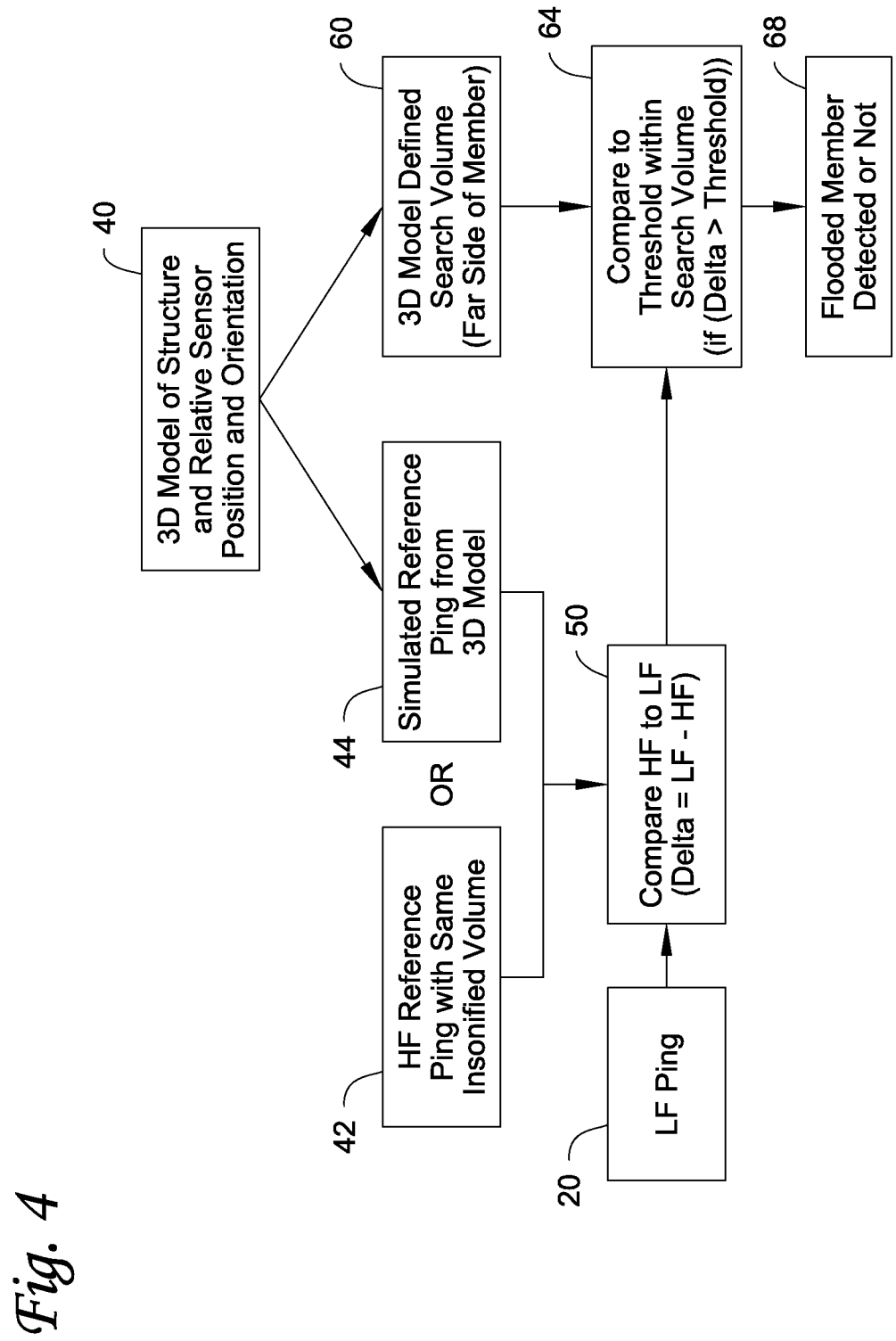
FIG. 4 is a flow chart depicting the flooded member detection method described herein.

FIG. 4 illustrates a flow chart of steps used to interpret the acoustic-structural return to determine whether the structural member is air filled or flooded. To interpret the acoustic-structural returns from the members 16, the position and orientation (pose information) of the sensor device 18 relative to a three-dimensional model of the support structure is used. The pose information and the existing three-dimensional model provide knowledge of which members 16 are supposed to be air filled and therefore in need of inspection, provide information on the structural member of interest such as its range from the sonar 18, the diameter of the member 16, and if there are other nearby structures possibly influencing the returned acoustic-structural waves and impacting the detected return. In addition, suitable software is provided to run an algorithm to compare the detected acoustic-structural return to an expected acoustic-structural return, i.e. an acoustic-structural return characteristic of an air filled or flooded member.

In FIG. 4, a three-dimensional model of the support structure and the pose of the sensor 18 relative to the three-dimensional model are obtained in step 40. The three-dimensional model can be any three-dimensional model of the support structure, pre-existing or generated in real-time using the methodology described in U.S. Provisional Patent Application Ser. No. 61/406,444, filed on Oct. 25, 2010, and titled Building A Three Dimensional Model Of An Underwater Structure, which is incorporated herein by reference in its entirety. The pose information can be provided by an inertial navigation system of known configuration associated with the sonar device, as well as employing the techniques disclosed in U.S. Provisional Patent Application Ser. No. 61/406,424, filed on Oct. 25, 2010, and titled Estimating Position and Orientation Of An Underwater Vehicle Relative To Underwater Structures, which is incorporated herein by reference in its entirety, to determine the pose relative to the three-dimensional model.

Next, for the structural member of interest, the expected acoustic-structural response is established. In the illustrated example, the expected acoustic-structural response is the expected acoustic-structural response assuming the underwater structural member of interest is air filled. However, in some circumstances, it is possible to establish the expected acoustic-structural response as if the underwater structural member of interest is flooded.

Two examples of establishing the expected acoustic-structural response assuming the structural member is air filled are as follows. First, a high frequency reference ping can be projected at the structural member of interest as shown at box 42 in FIG. 4. The high frequency reference ping can be generated from a second transducer of the sonar device 18 or by the same transducer if the sonar device is capable of different frequencies. The SeaKing Parametric SBP discussed above can generate a high frequency ping of 200 kHz in addition to the 20 kHz frequency ping. The high frequency wave does not penetrate the skin of the structural member, but instead reflects from the structural member similar to the first return of a low frequency wave reflecting from the skin/air interface as discussed above in FIG. 2A. Once processed, the detected acoustic-structural return forms the expected acoustic-structural response as if the structural member is air filled.

Another example of establishing the expected acoustic-structural response is to simulate a low frequency reference ping from the information obtained from the three-dimensional model of the structural member as shown at box 44 in FIG. 4. This can be accomplished by, assuming a certain ping intensity, calculating a return intensity with respect to time and an acoustic-structural response proportional to the exposed surface area 46 indicated in FIG. 5 with respect to range from the sonar device 18 at the low frequency. Other more complex sonar simulations could also be used.

Figure 8:
FIG. 8 illustrates the envelope of a reference return acoustic wave (i.e. acoustic-structural response) that is generated as if the structural member were air filled.

FIG. 8 illustrates an example of an expected acoustic-structural response 48 that has been established as if the member were air filled.

Figure 6:
FIG. 6 illustrates an example of the envelope of a return acoustic wave (i.e. acoustic-structural response) from an air filled member.
Figure 7:
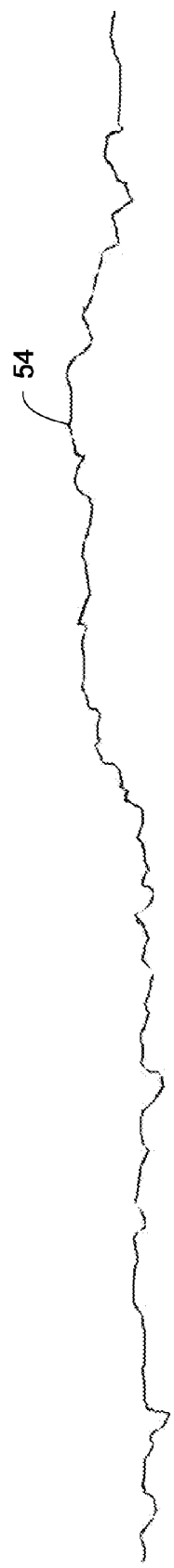
FIG. 7 illustrates an example of the envelope of a return acoustic wave (i.e. acoustic-structural response) from a flooded member.

Returning to FIG. 4, in step 50 the expected acoustic-structural response 48 is then compared to the acoustic-structural response determined from the actual detected return acoustic-structural response resulting from the low frequency acoustic wave 20 of the sonar system 18 by determining the difference between the two. FIG. 6 illustrates a detected return acoustic-structural response 52 from an air filled member (normalized for acoustic losses), and FIG. 7 illustrates a detected return acoustic-structural response 54 from a flooded member (normalized for acoustic losses).

Figure 9:
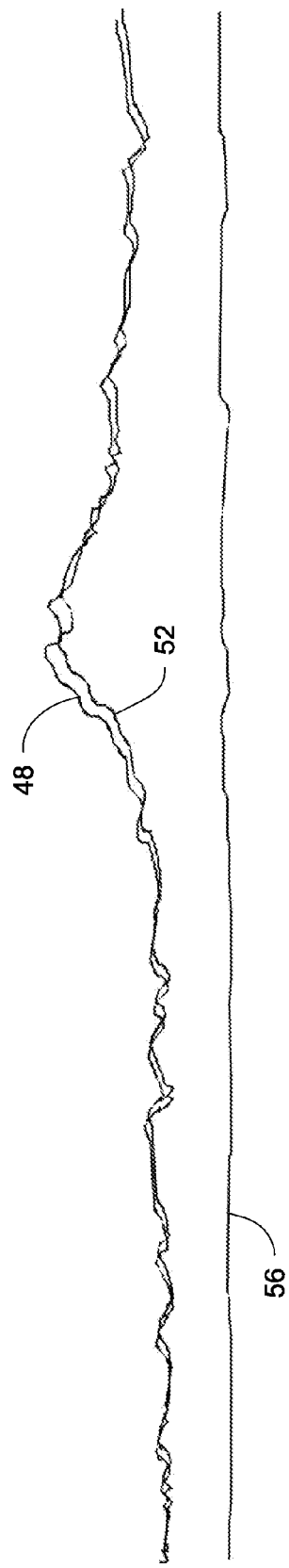
FIG. 9 illustrates determining the difference between the return acoustic wave envelope of FIG. 6 and the reference return acoustic wave envelope of FIG. 8.

FIG. 9 illustrates the expected return acoustic-structural response 48 relative to the air filled member detected return acoustic-structural response 52, with the differences 56 in magnitude (i.e. differences between the acoustic-structural features) between the two signals depicted underneath. Similarly, FIG. 10 illustrates the expected return acoustic-structural response 48 relative to the flooded member detected return acoustic-structural response 54, with the differences 58 in the magnitude (i.e. differences between the acoustic-structural features) between the two signals depicted underneath.

Figure 5:
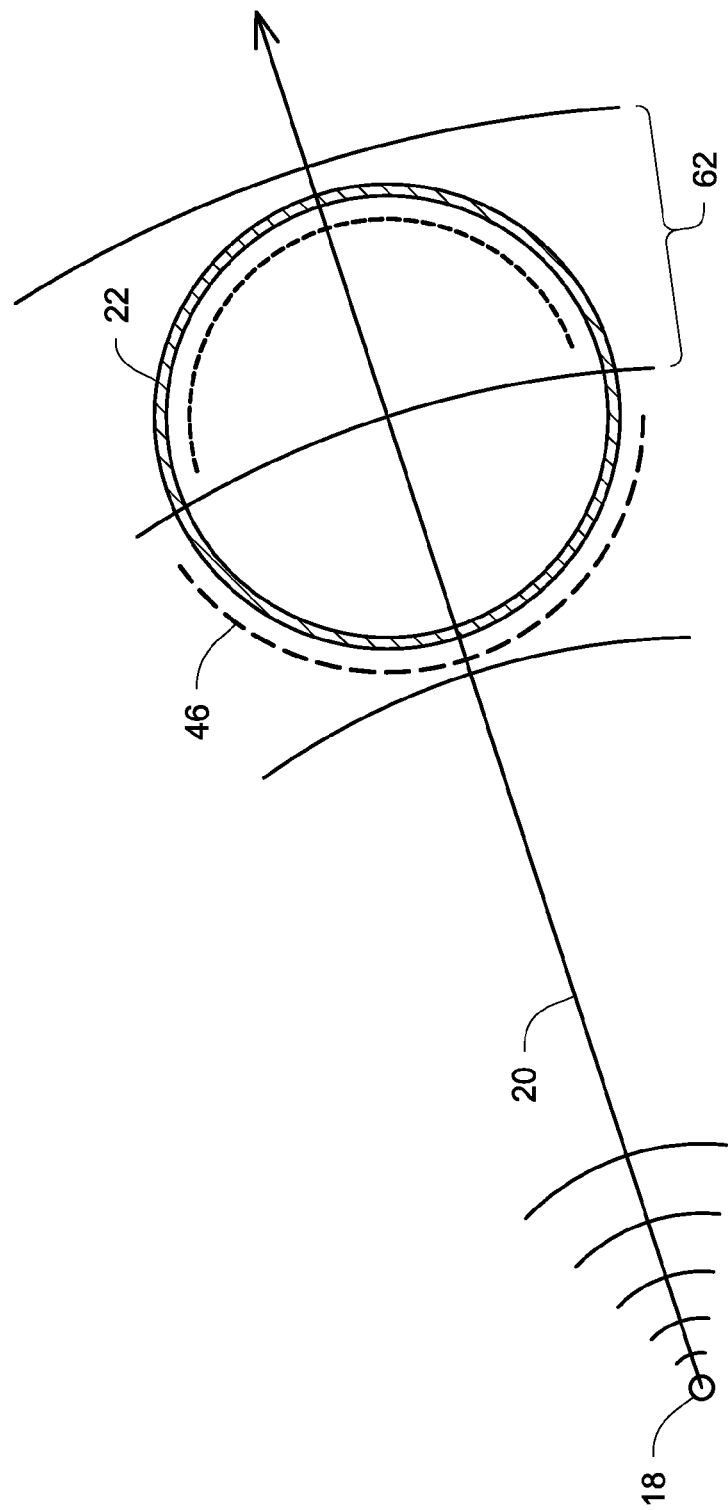
FIG. 5 depicts the concept of search volume used in the described method.

Returning to FIG. 4, another step includes defining a search volume from the three-dimensional model 60. With reference to FIG. 5, the search volume 62 is located at the far side of the member 16 and is calculated as the volume in which if a sonar return is received it would indicate a flooded member. The search volume in 3D space and translation into the time domain for the acoustic beam being analyzed conveys the information on the structural member in question such as the size, range, angle, and offset from the center of the acoustic beam. This information is needed if there are multiple objects in the path of the sonar's acoustic beam so that the processing algorithm can be focused and avoid false positives. The search volume represents the volume in which if a return is detected it must be due to a flooded member. The air of an air filled structural member would block the returns from the far side of the structural member or any objects immediately behind the structural member. This is why the search volume can extend slightly past the far side of the structural member.

Figure 10:
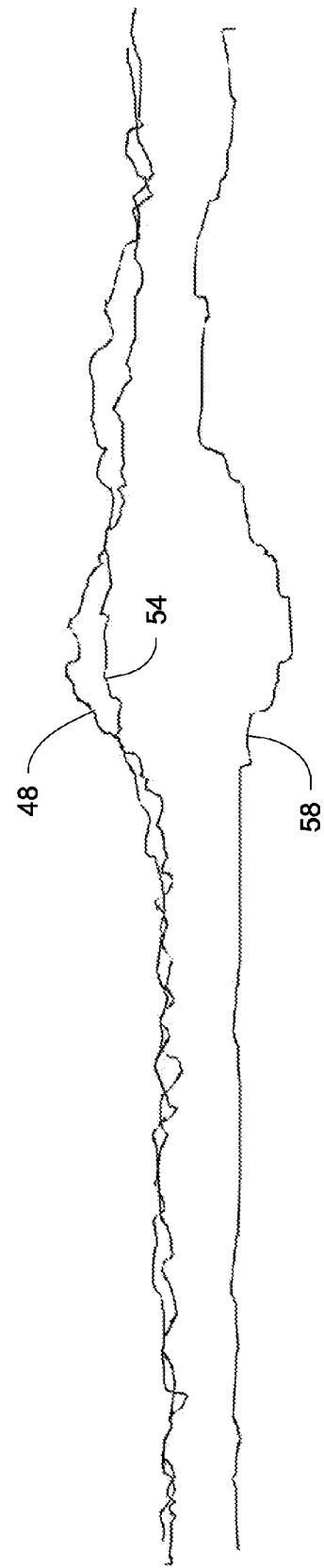
FIG. 10 illustrates determining the difference between the return acoustic wave envelope of FIG. 7 and the reference return acoustic wave envelope of FIG. 8.
Figure 11:
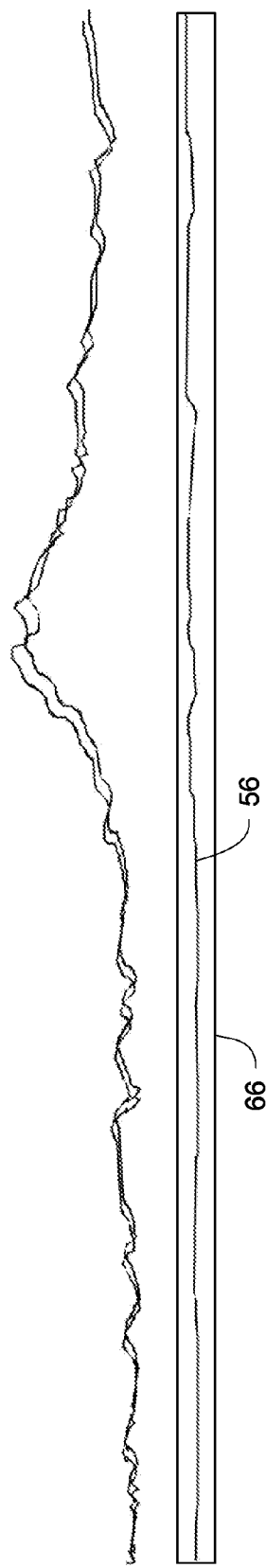
FIG. 11 illustrates comparing the difference determined in FIG. 9 to a threshold.
Figure 12:
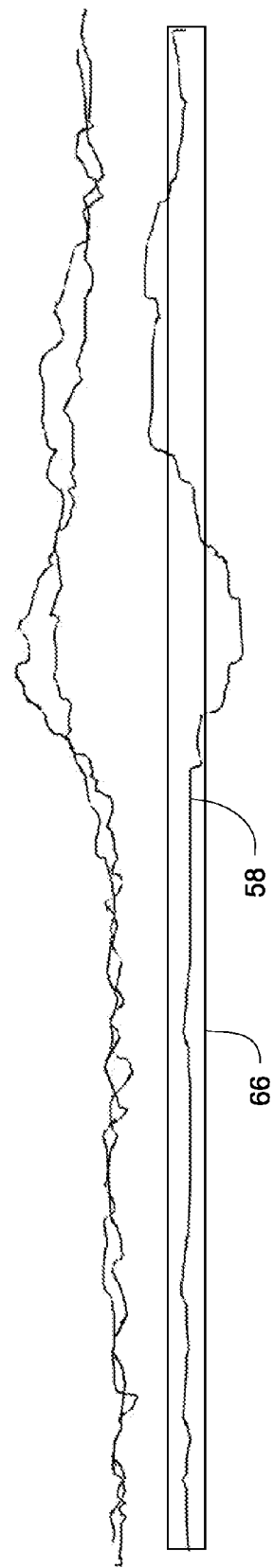
FIG. 12 illustrates comparing the difference determined in FIG. 10 to the threshold.

Returning to FIG. 4, another step 64 includes comparing the differences 56, 58 in magnitude and the acoustic-structural features from FIGS. 9 and 10 to a threshold within the search volume 62. This is depicted in FIGS. 11 and 12, with FIG. 11 showing the difference 56 in magnitudes relative to threshold 66 limits and FIG. 12 showing the difference 58 in magnitudes relative to the threshold 66 limits. The thresholds are arbitrary and in one example can be determined by experimentation with a given sonar system and range of possible structural members to inspect.

Returning to FIG. 4, based on the comparison in step 64, a decision is made as to whether or not the member of interest is flooded. As shown in FIG. 11, the difference 56 in magnitudes do not exceed the threshold limits. Therefore, the conclusion is drawn that the member of interest is not flooded but is instead air filled. FIG. 12 shows that the difference 58 in magnitudes exceed the threshold limits, i.e. portions of the magnitude differences (i.e. acoustic-structural feature differences 58) are outside the threshold limits box. Therefore, the conclusion is drawn from FIG. 12 that the member of interest is flooded.

The information that a member that is supposed to be air filled is instead flooded indicates that the member is cracked or otherwise damaged. This allows a diver, ROV, AUV or other inspection system to focus on the flooded member to aid in finding cracks or other damage, and effecting suitable repair or replacement of the damaged member.

Figure 13:
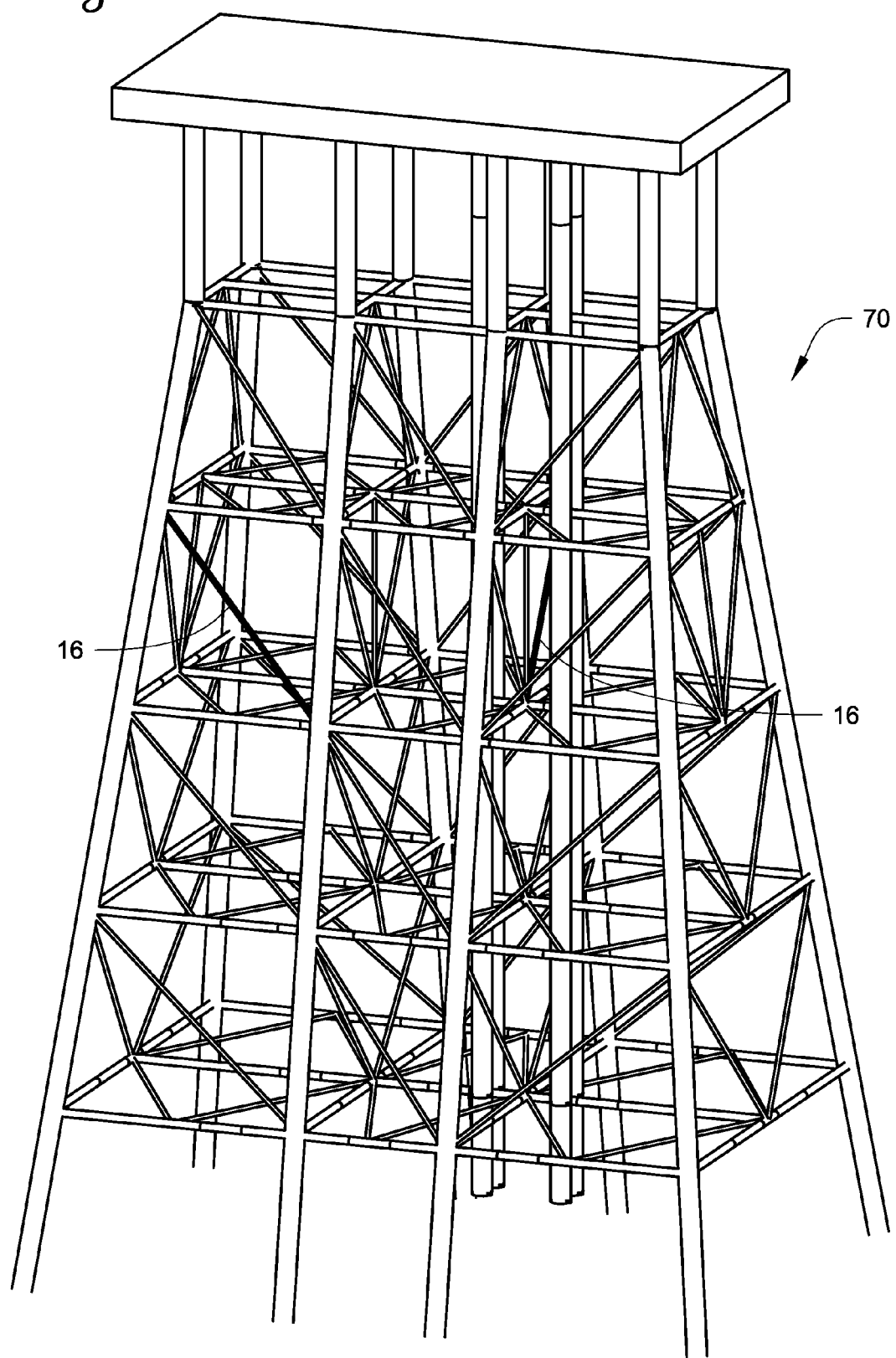
FIG. 13 illustrates the indication of flooded structural members on a three-dimensional model of the underwater support structure.

Optionally, as shown in FIG. 13, a flooded member(s) 16 that is detected can be indicated on a three-dimensional model 70 of the support structure, for example by highlighting the flooded members on the model 70 as shown in FIG. 13, to help show the extent of flooded members and help better understand the condition of the support structure.

Some structural members of underwater support structures may contain concentric tubes or other internal structures. The method described herein can be used to distinguish between an air filled structural member and a water filled structural member even if the structural member contains an arbitrary internal structure, as long as the arbitrary internal structure does not cause an otherwise air filled structural member to appear to be flooded.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A method of scanning an underwater support structure for flooded structural members, comprising:
   establishing an expected return acoustic-structural response by directing a reference acoustic wave at an underwater structural member of interest that forms part of the underwater support structure and detecting the resulting return acoustic-structural response;
   directing an inspection acoustic wave at the underwater structural member of interest from a source that is positioned at a distance from the underwater structural member of interest;
   detecting a return acoustic-structural response resulting from the inspection acoustic wave incident on the underwater structural member of interest;
   comparing the detected return acoustic-structural response with the expected return acoustic-structural response for the underwater structural member of interest; and
   based on the comparison, determining whether the underwater structural member of interest is flooded or not.

2. The method of claim 1, wherein the reference acoustic wave is at a frequency that is insufficient to penetrate a skin of the structural member of interest, and the inspection acoustic wave is at a frequency that is sufficient to penetrate the skin of the structural member of interest.

3. The method of claim 1, wherein the underwater support structure is associated with an offshore platform.

4. The method of claim 1, wherein comparing the detected return acoustic-structural response with the expected return acoustic-structural response comprises determining the position and orientation of the source relative to the underwater support structure.

5. The method of claim 4, further comprising establishing the expected return acoustic-structural response as if the underwater structural member of interest were air filled, determining the difference between the detected return acoustic-structural response and the expected return acoustic-structural response, and comparing the difference to a threshold.

6. The method of claim 1, comprising generating the reference acoustic wave using a first transducer and generating the inspection acoustic wave using a second transducer; or generating the reference acoustic wave and the inspection acoustic wave using the same transducer.

7. The method of claim 1, comprising generating the reference acoustic wave and the inspection acoustic wave using a parametric sonar.

8. A method, comprising:
   using a sonar system to determine if a structural member of an underwater support structure that is intended to be filled with air has flooded with water, the sonar system being spaced a distance from the structural member so that it is not in contact with the structural member;
   directing an inspection acoustic wave at the structural member using the sonar system and detecting a return acoustic-structural response resulting from the acoustic wave incident on the structural member, the inspection acoustic wave is at a frequency that is sufficient to penetrate a skin of the structural member;
   determining an expected return acoustic-structural response for the structural member by directing a reference acoustic wave at the structural member and detecting the resulting return acoustic-structural response, the reference acoustic wave is at a frequency that is insufficient to penetrate the skin of the structural member; and
   comparing the detected return acoustic-structural response with the expected return acoustic-structural response.

9. The method of claim 8, comprising generating the reference acoustic wave using a first transducer and generating the inspection acoustic wave using a second transducer; or generating the reference acoustic wave and the inspection acoustic wave using the same transducer.

10. The method of claim 8, wherein the sonar system is a parametric sonar that generates the reference acoustic wave and the inspection acoustic wave.

11. The method of claim 8, wherein the underwater support structure is associated with an offshore platform.

12. The method of claim 8, wherein comparing the detected return acoustic-structural response with the expected return acoustic-structural response comprises determining the position and orientation of the sonar system relative to the underwater support structure.

13. The method of claim 12, further comprising determining the expected return acoustic-structural response as if the underwater structural member of interest were air filled, determining the difference between the detected return acoustic-structural response and the expected return acoustic-structural response, and comparing the difference to a threshold.

14. A method of scanning an underwater support structure for flooded structural members, comprising:
- establishing an expected return acoustic-structural response for an underwater structural member of interest that forms part of the underwater support structure, the expected return acoustic-structural response being in the form of a reference signal;
- directing an inspection acoustic wave at the underwater structural member of interest from a source that is positioned at a distance from the underwater structural member of interest;
- detecting a return acoustic-structural response resulting from the inspection acoustic wave incident on the underwater structural member of interest to generate a return signal;
- comparing the return signal with the reference signal for the underwater structural member of interest; and
- based on the comparison, determining whether the underwater structural member of interest is flooded or not.

15. The method of claim 14, wherein establishing the expected return acoustic-structural response comprises directing a reference acoustic wave at the underwater structural member of interest at a frequency that is insufficient to penetrate a skin of the structural member of interest, and the inspection acoustic wave is at a frequency that is sufficient to penetrate the skin of the structural member of interest.

16. The method of claim 15, comprising generating the reference acoustic wave using a first transducer and generating the inspection acoustic wave using a second transducer; or generating the reference acoustic wave and the inspection acoustic wave using the same transducer.

17. The method of claim 15, comprising generating the reference acoustic wave and the inspection acoustic wave using a parametric sonar.

18. The method of claim 14, wherein the underwater support structure is associated with an offshore platform.

19. The method of claim 14, further comprising determining the position and orientation of the source.

20. The method of claim 15, further comprising establishing the expected return acoustic-structural response as if the underwater structural member of interest were air filled, determining differences between the return signal and the reference signal, and comparing the differences to a threshold.

* * * * *